United States Patent [19]

Nishimura et al.

[11] Patent Number: 5,712,139
[45] Date of Patent: Jan. 27, 1998

[54] PYRANOSE OXIDASE, PYRANOSE OXIDASE GENE, NOVEL RECOMBINANT DNA AND PROCESS FOR PRODUCING PYRANOSE OXIDASE

[75] Inventors: Ikuko Nishimura; Kimiharu Okada; Tomoyuki Minamihara; Genshiro Kawai; Yasuji Koyama; Masaru Suzuki, all of Noda, Japan

[73] Assignee: Kikkoman Corporation, Noda, Japan

[21] Appl. No.: 734,925

[22] Filed: Oct. 22, 1996

Related U.S. Application Data

[62] Division of Ser. No. 568,428, Dec. 6, 1995.

[30] Foreign Application Priority Data

Dec. 7, 1994 [JP] Japan .................................. 6-304086
May 24, 1995 [JP] Japan .................................. 7-124835

[51] Int. Cl.[6] .................................................. C12N 9/04
[52] U.S. Cl. .................. 435/190; 435/189; 435/252.3; 435/252.33; 435/320.1; 536/23.1; 536/23.2; 536/23.74

[58] Field of Search ................ 435/190, 14; 536/23.1, 536/23.2, 23.74

[56] References Cited

U.S. PATENT DOCUMENTS

| | | | |
|---|---|---|---|
| 4,560,661 | 12/1985 | Katsumata et al. | 435/183 |
| 4,569,913 | 2/1986 | Koths et al. | 435/190 |
| 4,636,464 | 1/1987 | Nakanishi et al. | 435/14 |

*Primary Examiner*—Robert A. Wax
*Assistant Examiner*—Nashaat T. Nashed
*Attorney, Agent, or Firm*—Oblon, Spivak, McClelland, Maier & Neustadt, P.C.

[57] ABSTRACT

The invention relates to a novel pyranose oxidase, a pyranose oxidase gene, and a recombinant DNA, as well as a process for producing the pyranose oxidase by use of a microorganism carrying said recombinant DNA. The process of the invention enables efficient production of the novel pyranose oxidase.

6 Claims, 3 Drawing Sheets

○ 100 mM acetate buffer
◆ 100 mM potassium phosphate buffer
● 100 mM Tris_HCl buffer
◇ 100 mMMES-sodium hydroxide buffer
■ 100 mM HEPES-sodium hydroxide buffer
□ 100 mM TAPS-sodium hydroxide buffer
▲ 100 mM CHES-sodium hydroxide buffer
△ 100 mM CHAPS-sodium hydroxide buffer
* 100 mM dipotassium phosphate_potassium chloride buffer OPTIMUM pH

- ● 100 mM acetate buffer
- ◆ 100 mM potassium phosphate buffer
- ○ 100 mM Tris-HCl buffer
- ◇ 100 mM MES-sodium hydroxide buffer
- ■ 100 mM HEPES-sodium hydroxide buffer
- □ 100 mM TAPS-sodium hydroxide buffer
- ▲ 100 mM CHES-sodium hydroxide buffer

PYRANOSE OXIDASE, PYRANOSE OXIDASE GENE, NOVEL RECOMBINANT DNA AND PROCESS FOR PRODUCING PYRANOSE OXIDASE

This is a Division of application Ser. No. 08/568,428 filed on Dec. 6, 1995, now pending.

FIELD OF THE INVENTION

The present invention relates to a novel pyranose oxidase useful in methods of enzymatically measuring glucose and 1,5-anhydro-D-glucitol in the vicinity of neutrality.

BACKGROUND OF THE INVENTION

The pyranose oxidase is an enzyme catalyzing conversion of glucose as optimum substrate by oxidation into glucosone, and this enzyme can be used in methods of enzymatically measuring glucose in food, body fluid, etc. Further, it can also be used in methods of enzymatically measuring 1,5-anhydro-D-glucitol that is regarded as important as a marker in diagnosis of diabetes.

Conventionally, the pyranose oxidase has been produced by inoculating *Coriolus versicolor* into medium and recovering the enzyme from the culture (Japanese Patent Publication No. 12557/1990). In this production process, however, there are disadvantages such as low yield etc. Further, the optimum pH of the above pyranose oxidase lies in an acid range (pH 6.2), so a large amount of enzyme is required for quantification in the vicinity of neutrality.

Moreover, methods of purifying the above enzyme are limited because its stable pH range is 5 to 7.4.

SUMMARY OF THE INVENTION

The present invention has been made to solve these problems in the prior art, and the object of the present invention is to provide a novel pyranose oxidase and a means of producing the same.

As a result of their eager study, the inventors successfully isolated a gene coding for pyranose oxidase from *Coriolus versicolor* and determined the structure thereof. Further, the inventors obtained a recombinant DNA having said gene inserted into a vector DNA, and they found that the pyranose oxidase can be efficiently produced by culturing a microorganism of the genus Escherichia carrying said recombinant DNA, and also that the pyranose oxidase thus produced differs from the conventional pyranose oxidase in substrate specificity.

That is, the present first invention is a novel pyranose oxidase with the following physicochemical properties:

(1) action: oxidizing glucose into glucosone;
(2) stable pH: pH 4.0 to 8.0;
(3) optimum pH: pH 7 to 7.5;
(4) optimum temperature: around 50° C.;
(5) stable temperature: stable at about 50° C. or less;
(6) substrate specificity: acting specifically on glucose, and acting on galactose, L-sorbose, D-xylose and 1,5-anhydro-D-glucitol;
(7) molecular weight: about 290,000 (gel filtration): the present second invention is a novel pyranose oxidase with the amino acid sequence of SEQ ID No. 2; the present third invention is a novel pyranose oxidase with an amino acid sequence bringing about the enzymatic activity of pyranose oxidase and set forth in SEQ ID No. 2 in which at least one amino acid has been added, deleted or replaced; the present forth invention is a pyranose oxidase gene coding for the amino acid sequence of SEQ ID No. 2; the present fifth invention is a pyranose oxidase gene coding for an amino acid sequence bringing about the enzymatic activity of pyranose oxidase and set forth in SEQ ID No. 2 in which at least one amino acid has been added, deleted or replaced;

the present sixth invention is a novel recombinant DNA having said pyranose oxidase gene inserted into a vector DNA; and the present seventh invention is a process for producing pyranose oxidase by culturing a microorganism carrying said recombinant DNA and recovering pyranose oxidase from the culture.

According to the present invention, the novel pyranose oxidase can be efficiently produced.

DETAILED DESCRIPTION OF THE INVENTION

Figure 1:
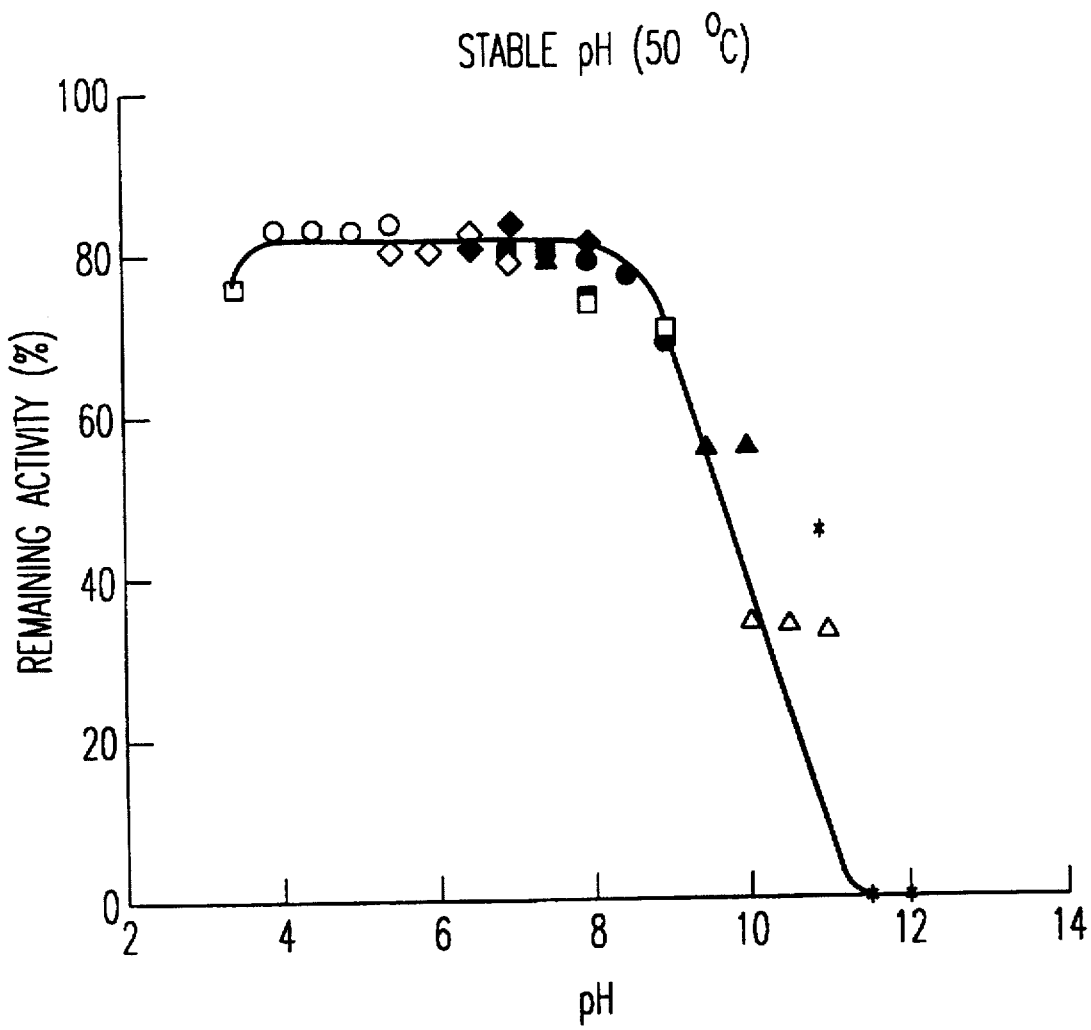
FIG. 1 shows the stable pH range of the present enzyme.

The pyranose oxidase gene of the present invention can be isolated in the following manner.

*Coriolus versicolor* ps4a (MAFF 420002 available from the gene bank of National Institute of Agrobiological Research, Ministry of Agriculture, Forestry and Fisheries, Japan) is cultured in a manner as described in e.g. Agric. Biol. Chem., 48, 2463–2470. The microorganism thus cultured are extracted to prepare mRNA in a manner as described in e.g. Molecular Cloning (Cold Spring Harbor Laboratory Press, 1989), 7.19–7.22.

The mRNA is used to synthesize cDNA by methods described in e.g. Mol. Cell. Biol., 2, 161 (1982) and Gene, 25, 263 (1983). Then, an Eco RI adaptor is attached to the resulting cDNA using e.g. cDNA rapid adaptor ligation module (Amersham).

The plasmid vector DNA used in the present invention includes e.g. bacteriophage vector DNA, plasmid vector DNA, etc., and a preferable example is plasmid pUC119 (Takara Shuzo Co., Ltd.). The plasmid vector DNA is digested with e.g. Eco RI (Takara Shuzo Co., Ltd.) if necessary followed by ethanol precipitation etc., whereby the plasmid vector capable of incorporating an Eco RI fragment as obtained as Eco RI digest.

This Eco RI digest is ligated to the above Eco RI adaptor-attached, gene-containing cDNA by the action of e.g. T4 DNA ligase (Boehringer Mannheim) to give a recombinant plasmid DNA.

This recombinant DNA is transformed into recipient microorganism such as *E. coli* K12, preferably *E. coli* JM109 (Takara Shuzo Co., Ltd.), XL1-Blue (Funakoshi), etc.

The resulting transformant colonies carrying various gene fragments are then screened by colony hybridization as described in Unit 6.4 in Current Protocols in Molecular Biology (WILEY Interscience, 1988). In this hybridization, an oligonucleotide prepared by labeling with $[\gamma\text{-}^{32}\text{P}]\text{ATP}$ (Amersham Japan) the terminal of the gene fragment obtained in Example 1, item (3), in the presence of T4 polynucleotide kinase (Takara Shuzo Co., Ltd.) is used as a probe for a recombinant DNA carrying the target gene.

The selected transformant carrying the pyranose oxidase gene is then subjected to CsCl density-gradient ultracentrifugation etc. to give the purified recombinant plasmid DNA.

This purified recombinant plasmid DNA is used to analyze the whole nucleotide sequence of the pyranose oxidase gene by such a method as described in Example 1, item (4), and the amino acid sequence encoded thereby is then determined. The amino acid sequence thus determined is shown in SEQ ID No. 2. The gene coding for the amino acid sequence thus determined is the pyranose oxidase gene of the present invention.

Because the above recombinant DNA lacks a promoter for expression in E. coli, E. coli transformed with it does not produce pyranose oxidase. Hence, it is necessary to prepare a pyranose oxidase-producing strain in the following manner.

Two kinds of oligonucleotides containing respectively the C- and N-terminals of the pyranose oxidase gene and their preceding and following regions each consisting of about 20 bases are prepared as primers (an oligonucleotide of 46 bases in total, the C terminal side is a complementary chain). These synthetic primers are designed to have an Nde I site so that the product amplified in polymerase chain reaction (referred to hereinafter as "PCR" ) gives only the coding region upon digestion with Nde I (Takara Shuzo Co., Ltd.). In the PCR, the above purified recombinant plasmid DNA is used as template and the above 2 kinds of oligonucleotides as primers.

Various methods can be used to prepare the DNA coding for that amino acid sequence of SEQ ID No. 2 in which at least one amino acid has been added, deleted or replaced. Examples of such methods involve treating the gene with a mutagen to cause point mutation or deletion mutation; selectively cleaving the gene, then deleting or adding a selected nucleotide, and linking the cleaved sites; inducing oligonucleotide mutation; or conducting PCR as described in Example 2.

The resulting DNA is inserted into a vector DNA containing a region involved in expression regulation including a promoter, an operator, a ribosome-binding site, etc., derived from E. coli lactose operon etc. (see The Operon, p. 227, Cold Spring Harbor Laboratory, 1980). The vector DNA used may be plasmid DNA and bacteriophage DNA. An example is vector pUTE500K' DNA used in Example 1, item (5). The resulting recombinant DNA is used to transform or transduce e.g. E. coli K-12, preferably E. coli JM109 (Takara Shuzo Co., Ltd.), XL1-Blue (Funakoshi) etc. so that transformants of each bacterial strain are obtained.

Transformation can be effected as described e.g. by D. M. Morrison in Methods in Enzymology, 68, 326–331 (1979), and transduction e.g. by B. Hohn in Methods in Enzymology, 68, 299–309 (1979).

The resulting strain belonging to the genus Escherichia capable of producing pyranose oxidase can be cultured in the following manner to produce pyranose oxidase.

The above microorganism is cultured in conventional solid medium, preferably in liquid medium.

Such medium is the one prepared by adding one or more inorganic salts selected from potassium dihydrogen phosphate, dipotassium hydrogen phosphate, magnesium sulfate, ferric chloride, ferric sulfate, manganese sulfate, etc., and if necessary sugars or carbohydrates and vitamins, to one or more nitrogen sources selected from yeast extract, peptone, meat extract, corn steep liquor, exudate of soybean or of wheat bran, etc.

It is preferable that the medium is initially adjusted within the range of pH 7 to 9. Culture is continued for 6 to 24 hours at a temperature of 20° to 37° C., preferably around 30° C., in submerged spinner culture under aeration, shake culture, stationary culture, etc. After culture was concluded, the pyranose oxidase can be recovered from the culture using the conventional recovery means known in the art.

The separation of the microorganism from the culture is conducted by filtration, centrifugation, etc. The microorganism thus collected are washed and then disrupted mechanically by ultrasonication, French press, dynamill, etc.; the microorganism cells are lyzed with lytic enzyme such as lysozyme; or the enzyme is extracted from the microorganism with a surface-active agent such as Triton X-100.

The crude enzyme solution thus obtained can be subjected to conventional purification means such as salting-out with ammonium sulfate, precipitation with organic solvent, ion-exchange chromatography, gel filtration chromatography, adsorption chromatography, electrophoresis, isoelectric precipitation, etc. These means are used in suitable combination to purify pyranose oxidase.

The physicochemical properties of the pyranose oxidase thus obtained are as follows:

(1) action: oxidizing glucose into glucosone;
(2) substrate specificity: acting specifically on glucose, and acting on galactose, L-sorbose, D-xylose, and 1,5-anhydro-D-glucitol;
(3) stable pH: pH 4.0 to 8.0;
(4) optimum pH: pH 7 to 7.5;
(5) optimum temperature: around 50° C.;
(6) stable temperature: stable at about 50° C. or less;
(7) molecular weight: about 290,000 (gel filtration).

In comparison of these physicochemical properties with those of the conventional pyranose oxidase, the present enzyme was found to be a novel enzyme from the fact that there is not known any enzyme such as the present enzyme that acts with high activity on 1,5-anhydro-D-glucitol.

EXAMPLES

The present invention is described in more detail by reference to the following examples, which however are not intended to limit the present invention.

Example 1

(1) Preparation of RNA from Coriolus versicolor ps4a

Coriolus versicolor ps4a (MAFF 420002 available from the gene bank of National Institute of Agrobiological Research, Ministry of Agriculture, Forestry and Fisheries, Japan) was inoculated into 200 ml medium (2% glucose, 0.5% yeast extract, 1.0% malt extract, 0.1% $K_2HPO_4$, 0.01% $Mg_2SO_4 \cdot 7H_2O$, 0.001% $FeCl_3 \cdot 6H_2O$) and cultured at 28° C. for 7 days under shaking. Then, the culture was filtered through a gauze.

16 g of the microorganism thus collected were immediately frozen in liquid nitrogen and then transferred to a mortar containing liquid nitrogen where the microorganism were then disrupted. The disrupted microorganism were transferred to another mortar immediately after the liquid nitrogen was evaporated. 45 ml guanidium solution [5 M guanidine thiocyanate, 50 mM Tris-HCl (pH 7.5), 10 mM EDTA, 5% (v/v) 2-mercaptoethanol, 4% (w/v) N-lauroylsarcosinate] was added to it.

After sufficiently stirred in the mortar until the viscosity was lowered, the microorganism solution was centrifuged at 10,000 r.p.m., 4° C. for 15 minutes. CsCl was added to the supernatant in an amount of 0.4 g/ml. The supernatant was centrifuged at 15,000 r.p.m., 4° C. for 10 minutes and then layered on a CsCl cushion (5.7 M CsCl, 100 mM EDTA) to be subjected to density-gradient centrifugation (32000 r.p.m., 15° C., 24 hours). The RNA thus obtained as precipitates was washed with ethanol to remove excess CsCl, dissolved in water, and precipitated with ethanol. 1050 µg purified RNA was thus obtained. 20 µg mRNA was obtained from the RNA by purification with Oligotex-dT30 <Super> (Takara Shuzo Co., Ltd.)

(2) Preparation of a cDNA library

The cDNA was synthesized using cDNA Synthesis Plus (Amersham) from 4 µg of the above mRNA. An Eco RI adaptor was attached to the cDNA using cDNA rapid adaptor ligation module (Amersham). The resulting DNA was ligated to 100 ng of a separately prepared Eco RI digest of plasmid vector DNA pUC119 (Takara Shuzo Co., Ltd.) by the action of 1 U of T4 DNA ligase (Boehringer Mannheim). The recombinant plasmid DNA thus obtained was transformed into *E. coli* XL1-Blue strain (Funakoshi) as described by D. M. Morrison in Methods in Enzymology, 68, 326–331 (1979). As a result, 5 x $10^3$ colonies were obtained. They were then blotted onto a nylon membrane filter Hybond-N⁺(Amersham) according to the manufacture's instruction.

(3) Isolation of the pyranose oxidase gene by colony hybridization

Pyranose oxidase was purified from cultured Coriolus versicolor ps4a by ammonium sulfate precipitation, polyethylene imine cellulose, QAE Sephadex and HPLC, and its N-terminal amino acid sequence was determined. The N-terminal amino acid sequence was Lys Val Pro Gly Met Asp Ile Lys Tyr Asp Val Val Ile Val Gly.

1 mg of the purified pyranose oxidase was fragmented by treatment with lysyl endopeptidase and an partial amino acid sequence in the protein was determined. The partial amino acid sequence thus determined was Met Asp Ile Lys Tyr Asp Val. Then, the polynucleotide (SEQ ID 40:6) AC(A/G) TC(A/G)TA(T/C)TT(A/G/T)AT(A/G)TCCAT (where A is adenine, C cytosine, G guanine, T thymine, A/G adenine or guanine, T/C thymine or cytosine, and A/G/T adenine, guanine or thymine), which corresponds to said partial amino acid sequence, was synthesized in a DNA synthesizer model 392 (Applied Biosystems).

10 pmoles of this synthetic DNA was end-labeled with [γ-³²P]ATP (Amersham Japan) in the presence of T4 polynucleotide kinase (Takara Shuzo Co., Ltd.). It was used a probe for colony hybridization. Colony hybridization was conducted in the manner as described in Unit 6.4 of Current Protocols in Molecular Biology (WILEY Interscience, 1988). One positive colony was obtained. A plasmid DNA (pPR343EO) carrying the pyranose oxidase gene was prepared from this positive clone by ultracentrifugation.

(4) Analysis of the pyranose oxidase gene

After the plasmid DNA (pPR343EO) was cleaved with Eco RI, it was found that about 2.1 kb cDNA fragment had been inserted into it. This plasmid DNA was sequenced with a kilo-sequence deletion kit (Takara Shuzo Co., Ltd.) using a 373A DNA sequencing system (Applied Biosystems). The result indicated that it contains the whole-length cDNA for pyranose oxidase. The determined nucleotide sequence of the cDNA for pyranose oxidase is shown in SEQ ID No: 1 and the amino acid sequence encoded thereby in SEQ ID No: 2. The open reading frame in the cDNA for pyranose oxidase was found to consist of 1869 bp (623 amino acids).

(5) Construction of expression vector pUTE500K'

Plasmid vector pBR322 DNA (Takara Shuzo Co., Ltd.) was digested with Nde I and made blunt-ended using a DNA blunting kit (Takara Shuzo Co., Ltd.). The Nde I site was eliminated by cyclizing the vector DNA again with T4 DNA ligase (Boehringer Mannheim). Then, this vector was digested with Eco RI and Nru I, then blunt-ended using the above DNA blunting kit, and electrophoresed on agarose gel, and an about 3.4 kb DNA fragment containing the origin of replication was obtained using GENECLEAN II kit (Funakoshi). This DNA was cyclized with T4 DNA ligase and then linearized by cleavage with Eco RI to give an Eco RI fragment.

The following DNA sequence containing a region involved in expression regulation including a promoter, an operator, a ribosome-binding site, a terminator, etc., derived from *E. coli* lactose operon etc., an Nde I site, and a binding site for a sequencing primer (–21M13 Forward Primer) (see The Operon, p. 227, Cold Spring Harbor Laboratory, 1980):

```
AATTCGGTACCGGATCCGCTAGCTTTACATTATGCTTCCGGCTCGTATAA
    GCCATGGCCTAGGCGATCCAAATGTAATACGAAGGCCGACCATATT
TGTGTGGAATTGTGAGCGGATAACAATTTCACACAGGAGGTTTCATATGC
ACACACCTTAACACTCGCCTATTGTTAAAGTGTGTCCTCCAAAGTATACG
ATTGATCATTAATTAATAGCCCGCCTAATGACCGGGCTTTTTTTTACTAG
TAACTACTAATTAATTATCGGGCGGATTACTCGCCCGAAAAAAAATGATC
TAGATCTCTGGCCGTCGTTTTACAGTCGACGGTACCG
ATCTAGAGACCGGCAGCAAAATGTCAGCTGCCATGGCTTAA
``` was synthesized in a DNA synthesizer model 392 (Applied Biosystems) and then linked to the Eco RI fragment prepared above whereby an expression vector pUTE500 was obtained. The expression vector pUTE500 was then digested with Sal I, and a kanamycin resistant gene (Pharmacia), cleaved at Sal I site, was then attached thereto whereby an expression vector pUTE500K'. was obtained.

(6) Preparation of *E. coli* XL1-Blue (pPRME10)

An oligonucleotide (SEQ ID No: 3) containing the N-terminal of the pyranose oxidase gene and its preceding and following regions each consisting of about 20 bases, and an oligonucleotide (SEQ ID No: 4) containing the C-terminal and its preceding and following regions each consisting of about 20 bases were synthesized respectively as primers in DNA synthesizer model 392 (Applied Biosystems). These primers were designed to have an Nde I site so that only the coding region is obtained by digesting with Nde I the product amplified in PCR.

These primers were used in PCR with the above Eco RI digest of the plasmid DNA (pPR343EO) as template and a GeneAmp DNA PCR reagent kit (Takara Shuzo Co., Ltd.) to amplify DNA containing the coding region for pyranose oxidase. The resulting DNA was digested with Nde I and then inserted into the Nde I site of the above expression plasmid vector pUTE500K' whereby recombinant plasmid pPRME10 DNA was obtained.

The recombinant plasmid DNA pPRME10 was transformed into *E. coli* XL1-Blue (Funakoshi) according to the D. M. Morrison method (Methods in Enzymology, 68, 326–331, 1979) whereby a transformant, *E. coli* XL1-Blue (pPRME10), was obtained. The *E. coli* XL1-Blue (pPRME10) has been deposited as FERM BP-4831 with the National Institute of Bioscience and Human-Technology, Agency of Industrial Science and Technology, Japan.

The resulting *E. coli* XL1-Blue (pPRME10) was cultured for 16 hours under shaking in TY medium (1% Bactotrypton, 0.5% Bactoyeast extract, 0.5% NaCl, pH 7.0) containing 1 mM isopropyl-β-D-thiogalactopyranoside. The pyranose oxidase activity, determined on the basis of the formation of hydrogen peroxide, was 0.1 U/ml.

Example 2

The oligonucleotide of SEQ ID No: 5 and the oligonucleotide of SEQ ID No: 4 were synthesized as primers in a DNA synthesizer model 392 (Applied Biosystems). These primers were used together with the above Eco RI digest of the plasmid DNA (pPR343EO) obtained in Example 1, item (3) as template to carry out PCR using GeneAmp DNA PCR reagent kit (Takara Shuzo Co., Ltd.). The product amplified was digested with Nde I to prepare DNA coding for that amino acid sequence of SEQ ID No. 2 which lacked the amino acids from Ser at the 2-position to Lys at the 38-position. This DNA was inserted into the Nde I site in the above expression plasmid vector pUTE500K' DNA whereby recombinant plasmid pPRME18 DNA was obtained.

The recombinant plasmid pPRME18 was transformed into *E. coli* XL1-Blue (Funakoshi) according to the D. M. Morrison method (Methods in Enzymology, 68, 326–331, 1979) whereby a transformant *E. coli* XL1-Blue (pPRME18) was obtained. The *E. coli* XL1-Blue (pPRME18) has been deposited as FERM BP-4832 with the National Institute of Bioscience and Human-Technology, Agency of Industrial Science and Technology, Japan.

The *E. coli* XL1-Blue (pPRME18) was cultured for 16 hours under shaking in TY medium (1% Bactotrypton, 0.5% Bactoyeast extract, 0.5 NaCl, pH 7.0) containing 1 mM isopropyl-β-D-thiogalactopyranoside. The pyranose oxidase activity, determined on the basis of the formation of hydrogen peroxide, was 0.01 U/ml.

Example 3

TY medium (1% Bactotrypton, 0.5% Bactoyeast extract, 0.5% sodium chloride, pH 7.0) was introduced into a flask and sterilized at 121° C. for 10 minutes. *E. coli* XL1-Blue (pPRME10) was inoculated into it and cultured for 14 hours under shaking in an incubator.

Then, 100 ml of the above culture was inoculated into a 30-liters jar fermentor containing 20 liters of the above-described TY medium (sterilized under the same conditions as above) containing 1 mM isopropyl-β-D-thiogalactopyranoside. The microorganism were cultured for about 16 hours aerobically at an aeration rate of 10 L/min. under shaking at 300 r.p.m. The pyranose oxidase activity after cultivation, determined on the basis of the formation of hydrogen peroxide, was 0.3 U/ml.

After cultivation was concluded, microorganism were recovered from 40 liters of the liquid culture (20 liters x 2) through an ultrafiltration membrane (AHV-3010) produced by Asahi Chemical Industry Co., Ltd., and the microorganism were washed with tap water and concentrated to about 10 liters.

Step 1 (Preparation of crude enzyme solution): 5 g egg lysozyme, i liter of 0.55 M EDTA 2Na, pH 8.0 and 1 liter of 0.11 M potassium phosphate buffer, pH 8.0, were added to the above concentrate of microorganism. The mixture was allowed to stand at 37° C. for 24 hours. The microorganism were then lyzed by freeze-thawing. 5% aqueous protamine solution (pH 8.0) was added dropwide to the lyzed solution to remove nucleic acids. The supernatant was dialyzed in an ultrafiltration membrane against 10 mM potassium phosphate buffer (pH 7.5) containing 50 mM potassium chloride and concentrated into an about 500 ml crude enzyme solution.

Step 2 (Heat treatment): The above dialyzate (about 500 ml) was heated and kept in a water bath at 47.5° C. for 30 minutes for denaturization of the protein contaminants present. After heat treatment, the denatured proteins were removed by a refrigerating centrifuge (CR22 manufactured by Hitachi). The resulting supernatant, 490 ml, was dialyzed through an ultrafiltration membrane against 10 mM potassium phosphate buffer (pH 7.0) containing 50 mM potassium chloride, whereby an enzyme solution, about 500 ml, was obtained.

Step 3 (DEAE-cellulose treatment):. DEAE-cellulose resin (wet weight: about 1 kg) was added to about 500 ml of the enzyme solution, and they were mixed so that the enzyme was adsorbed onto the resin. The DEAE-cellulose was washed with 10 mM potassium phosphate buffer (pH 7.0) containing 50 mM potassium chloride, and the enzyme was eluted with 10 mM potassium phosphate buffer (pH 7.0) containing 0.5 M potassium chloride. The eluate was dialyzed in an ultrafiltration membrane against 10 mM potassium phosphate buffer (pH 7.0) containing 50 mM potassium chloride and concentrated into about 500 ml enzyme solution.

Step 4 (QAS-Sephadex A-50 column chromatography): The enzyme solution (500 ml) was adsorbed onto QAE-Sephadex A-50 column (7.8 x 40 cm). After the column was washed with 10 mM potassium phosphate buffer (pH 7.0) containing 0.26 M potassium chloride, the enzyme was eluted with 10 mM potassium phosphate buffer (pH 7.0) containing 0.28 M potassium chloride.

As a result of the above purification procedures, 150 mg enzyme preparation of not less than 90% purity (about 3000 U, 20 U/mg protein) was obtained.

Example 4

The enzyme of the present invention obtained in Example 3 was examined for the following items.

(1) Measurement of titer 3.0 ml of an enzyme-containing solution consisting of 1.0 ml of 0.1M Tris-HC1 buffer, pH 7.0, 0.2 ml of a color-producing solution (prepared by adding 2000 U peroxidase to 100 ml of 0.1 M Tris-HCl buffer, pH 7.0 containing 10 mM 4-aminoantipyrine and 10 mM phenol), 0.1 ml of 1M glucose, 0.1 ml pyranose oxidase solution and 1.6 ml water was allowed to react at 37° C., and the increase in absorbance at 500 nm was determined with U2000 double beam spectrophotometer (manufactured by Hitachi, Ltd.).

One unit of enzyme activity is defined as the amount of enzyme which causes formation of 1 μmol of hydrogen peroxide per minute at 37° C., pH 7.0. The calculation of liter was carried out using the following equation assuming that the molecular extinction coefficient of the quinoimine pigment formed under the above conditions is $5.3 \times 10^3$:

Enzyme activity: $(\Delta A_{500}/5.3) \times (3.0/0.1) \times$ dilution degree of enzyme.

In the equation, $\Delta A_{500}$ means the increase in absorbance at 500 nm per unit time (1 minute).

(2) Stable pH and optimum pH range

Stable pH was determined by measuring the remaining activity after treatment at pH 3.5 to 12.0 at 50° C. for 30 minutes in the following buffers: 100 mM acetate buffer (pH 3.5 to 5.5), 100 mM MES-sodium hydroxde buffer (pH 5.5 to 7.0), 100 mM HEPES-sodium hydroxide buffer (pH 7.0 to 8.0), 100 mM TAPS-sodium hydroxide buffer (pH 8.0 to 9.0), 100 mM CHES-sodium hydroxide buffer (pH 9.0 to 10.0), 100 mM CHAPS-sodium hydroxide buffer (pH 10.0 to 11.0), 100 mM dipotassium phosphate-potassium chloride buffer (pH 11.0 to 12.0), 100 mM potassium phosphate buffer (pH 6.5 to 8.0), and 100 mM Tris-HCl buffer (pH 7.5 to 9.0). The results are shown in FIG. 1. The stable pH of the present enzyme ranges from pH 4.0 to 8.0.

Figure 2:
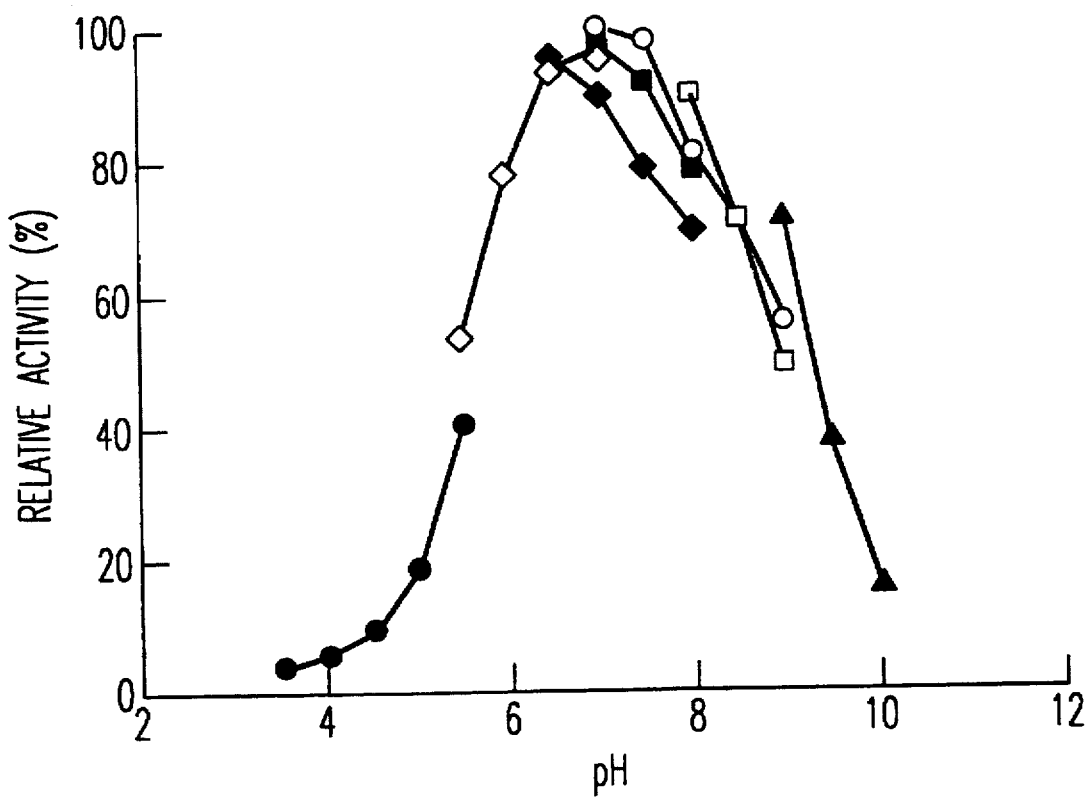
FIG. 2 shows the optimum pH of the present enzyme.

Optimum pH was determined by measuring the activity of the present enzyme at each pH in the following buffers: 100 mM acetate buffer (pH 3.5 to 5.5), 100 mM MES-sodium hydroxide buffer (pH 5.5 to 7.0), 100 mM HEPES-sodium hydroxide buffer (pH 7.0 to 8.0), 100 mM TAPS-sodium hydroxide buffer (pH 8.0 to 9.0), 100 mM CHES-sodium hydroxide buffer (pH 9.0 to 10.0), 100 mM potassium phosphate buffer (pH 6.5 to 8.0), and 100 mM Tris-HCl buffer (pH 7.5 to 9.0). The results are shown in FIG. 2. The optimum pH of the present enzyme lies in the vicinity of pH 7.0 to 7.5.

Figure 3:
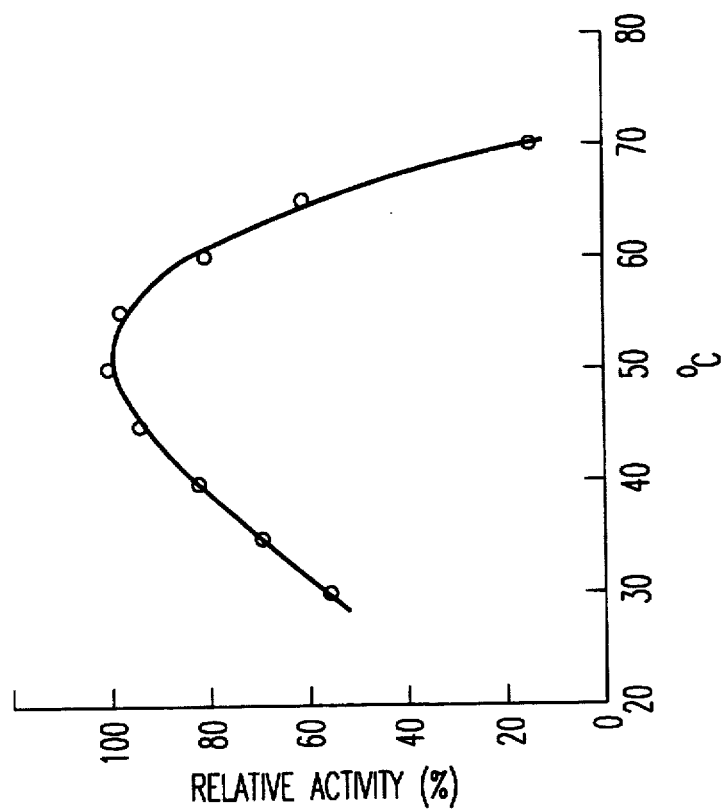
FIG. 3 shows the optimum temperature of the present enzyme.

(3) Optimum temperature 3.0 ml of an enzyme-containing solution consisting of 1.0 ml of 0.1 M Tris-HCl buffer (pH 7.0), 0.2 ml of the above-described color-producing solution, 0.1 ml of 1M glucose solution, 0.1 ml of 1.0 U/ml pyranose oxidase and 1.6 ml water was allowed to react at a predetermined temperature for 5 minutes in an incubator. The enzyme activity was determined by measuring the final absorbance at 500 nm in U2000 double beam spectrophotometer (Hitachi, Ltd.). As can be seen from FIG. 3, the optimum temperature of the present enzyme lies in about 50° C.

(4) Temperature stability

Figure 4:
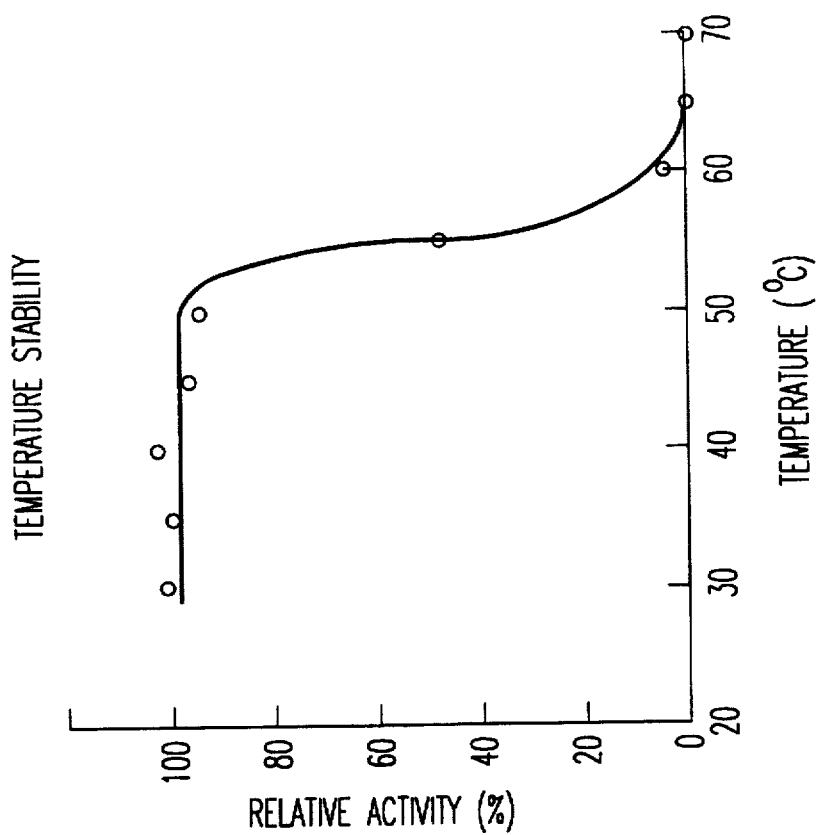
FIG. 4 shows the stable temperature range of the present enzyme.

An enzyme preparation (500 U/ml) was mixed in 100 mM Tris-HCl buffer, pH 8.0, in the ratio of 1 to 9, and the solution was kept for 30 minutes at a predetermined temperature as shown in FIG. 4. After cooling, the solution was diluted 50-fold with 100 mM Tris-HCl buffer, pH 7.0, and allowed to stand for 10 minutes at room temperature. Then, the remaining activity was determined. As is evident from FIG. 4, the present enzyme was stable at a temperature of up to about 50° C.

(5) Substrate specificity

For examination of the substrate specificity of the present enzyme, each of sugar solutions (0.1 M) shown in Table 1 was used in place of glucose in the method described in (1) above. 2.5 units of pyranose oxidase were added to the reaction solution. The activity for each substrate is shown in relative activity that is expressed relative to that (100%) for the substrate glucose.

TABLE 1

Substrate specificity of pyranose oxidase

| substrate (3.3 mM) | relative activity (%) |
|---|---|
| D-glucose | 100.0 |
| mannose | 0.2 |
| galactose | 3.2 |
| L-sorbose | 9.0 |
| lactose | 0 |
| D-xylose | 6.5 |
| maltose | 1.1 |
| trehalose | 0.1 |
| sucrose | 0 |
| mannitol | 0 |
| D-glucosamine | 0 |
| gluconic acid | 0.4 |
| fructose | 0 |
| xylitol | 0 |
| D-sorbitol | 0 |
| N-acetyl-D-glucosamine | 0 |
| 2-deoxy-D-glycose | 1.6 |
| D-gluconic acidδ lactone | 0.4 |
| raffinose | 0 |
| L-rhamnose | 0.1 |
| 1,5-anhydro-D-glucitol | 14.2 |

As can be seen from Table 1, the present enzyme shows high specificity for D-glucose but acts on galactose, D-xylose, and 1,5-anhydro-D-glucitol.

The Km value for D-glucose was determined to be 1.37 mM.

(6) Molecular weight

The molecular weight determined by gel filtration on TSK gel G3000SWXL (Tosoh Corporation) was about 290,000. The subunit of the present enzyme was found to have a molecular weight of about 64,000 by SDS-polyacrylamide gel electrophoresis on polyacrylamide gel with a 4 to 20% (W/V) density gradient of acrylamide gel (Multigel 4–20 produced by Daiichi Kagaku). Hence, it is estimated that the enzyme of the present invention is a tetramer of subunits.

What is claimed is:

1. An isolated DNA sequence encoding a pyranose oxidase and having the sequence of SEQ ID NO:1.

2. An isolated DNA sequence encoding a pyranose oxidase and comprising the sequence of SEQ ID NO:1.

3. A recombinant DNA having the DNA sequence of claim 1 inserted into a vector DNA.

4. A recombinant DNA having the DNA sequence of claim 2 inserted into a vector DNA.

5. A process of producing a pyranose oxidase, comprising:

culturing a microorganism belonging to the genus Escherichia transformed with the recombinant DNA of claim 3; and isolating the pyranose oxidase from the culture.

6. A process of producing a pyranose oxidase, comprising:

culturing a microorganism belonging to the genus Escherichia transformed with the recombinant DNA of claim 4; and isolating the pyranose oxidase from the culture.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 1869 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: E. coli ( x i ) SEQUENCE DESCRIPTION: SEQ ID NO:1:

```
ATGTCTACTA GCTCGAGCGA CCCGTTCTTC AACTTCACGA AGTCGAGCTT TAGGAGCGCG      60
GCGGCGCAGA AGGCCTCGGC GACTTCTCTG CCGCCGCTGC CTGGTCCCGA CAAGAAAGTC     120
CCTGGAATGG ACATCAAGTA CGACGTTGTC ATAGTAGGCT CCGGACCGAT TGGATGCACG     180
TATGCCCGTG AGCTCGTCGA AGCCGGTTAC AAGGTCGCCA TGTTCGACAT CGGGGAAATT     240
GACTCTGGCC TGAAGATCGG TGCCCACAAG AAGAACACCG TCGAATACCA GAAGAACATT     300
GACAAGTTTG TGAACGTCAT TCAGGGCCAA TTGATGTCTG TTTCCGTTCC CGTCAATACC     360
CTCGTGATCG ACACGCTCAG CCCGACGTCT TGGCAAGCTT CATCGTTCTT CGTCCGCAAT     420
GGCTCGAACC CAGAGCAGGA CCCGCTTCGT AACCTCAGTG GTCAGGCGGT CACGCGTGTC     480
GTCGGAGGCA TGTCCACGCA CTGGACATGC GCGACACCGC GCTTTGACCG CGAGCAGCGC     540
CCGTTGCTCG TGAAGGACGA CCAGGACGCT GACGACGCCG AGTGGGACCG GCTGTACACC     600
AAGGCCGAGT CATACTTCAA GACCGGGACG GACCAGTTCA AGGAGTCGAT CCGCCACAAC     660
CTCGTGCTCA ACAAGCTCGC GGAGGAATAC AAAGGTCAGC GCGACTTCCA GCAGATCCCG     720
CTCGCGGCAA CGCGTCGCAG TCCGACCTTC GTCGAGTGGA GCTCGGCGAA CACCGTGTTC     780
GACCTCCAGA ACAGGCCGAA CACGGACGCG CCGAATGAGC GCTTCAACCT CTTCCCCGCG     840
GTTGCATGTG AGCGCGTCGT GCGCAACACG TCGAACTCCG AGATCGAGAG TCTGCACATC     900
CACGACCTCA TCTCGGGCGA CCGCTTCGAA ATCAAAGCAG ACGTGTTCGT TCTTACAGCC     960
GGGGCGGTCC ACAACGCGCA GCTTCTCGTG AACTCTGGCT TTGGACAGCT GGGCCGGCCG    1020
GACCCCGCGA ACCCGCCGCA GTTGCTGCCG TCCCTGGGAA GCTACATCAC CGAGCAGTCG    1080
CTCGTCTTCT GCCAGACCGT GATGAGCACC GAGCTCATCG ACAGCGTCAA GTCCGACATG    1140
ATCATCAGGG GCAACCCTGG CGATCTGGGG TACAGCGTCA CGTACACGCC CGGCGCGGAG    1200
ACCAACAAGC ACCCGGACTG GTGGAACGAA AAGGTGAAGA ACCACATGAT GCAGCACCAG    1260
GAGGACCCGC TTCCAATCCC GTTCGAGGAC CCCGAGCCGC AGGTCACCAC CTTGTTCCAG    1320
CCATCGCACC CGTGGCACAC TCAGATTCAC CGCGATGCGT TCAGTTACGG CGCGGTGCAG    1380
CAAAGCATCG ACTCACGTCT CATCGTCGAC TGGCGCTTCT TCGGCCGGAC GGAGCCAAAG    1440
GAGGAGAACA AGCTCTGGTT CTCGGACAAA ATTACGGACA CGTACAACAT GCCGCAGCCG    1500
ACGTTCGACT TCCGCTTCCC GGCGGGCCGC ACGAGCAAGG AGGCGGAGGA CATGATGACC    1560
GATATGTGCG TTATGTCGGC GAAGATTGGT GGCTTCCTGC CCGGCTCCCT CCCGCAATTC    1620
ATGGAGCCCG GTCTTGTCCT TCACCTCGGT GGTACGCACC GCATGGGCTT CGACGAGCAG    1680
GAGGACAAGT GCTGCGTCAA CACGGACTCG CGCGTGTTTG GCTTCAAGAA CCTGTTCCTC    1740
GGTGGCTGCG GAAACATTCC CACCGCGTAC GGCGCGAACC CGACGCTCAC CGCAATGTCG    1800
CTCGCGATCA AGAGTTGCGA GTACATCAAG AACAACTTCA CACCGAGCCC TTTCACAGAT    1860
CAGGCTGAG                                                            1869
```

( 2 ) INFORMATION FOR SEQ ID NO:2:

( i ) SEQUENCE CHARACTERISTICS:
        ( A ) LENGTH: 623 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Ser Thr Ser Ser Ser Asp Pro Phe Phe Asn Phe Thr Lys Ser Ser
 1               5                  10                  15
```

```
Phe Arg Ser Ala Ala Ala Gln Lys Ala Ser Ala Thr Ser Leu Pro Pro
                    20                  25                  30
Leu Pro Gly Pro Asp Lys Lys Val Pro Gly Met Asp Ile Lys Tyr Asp
            35                  40                  45
Val Val Ile Val Gly Ser Gly Pro Ile Gly Cys Thr Tyr Ala Arg Glu
50                      55                  60
Leu Val Glu Ala Gly Tyr Lys Val Ala Met Phe Asp Ile Gly Glu Ile
65                      70                  75                  80
Asp Ser Gly Leu Lys Ile Gly Ala His Lys Lys Asn Thr Val Glu Tyr
                85                  90                  95
Gln Lys Asn Ile Asp Lys Phe Val Asn Val Ile Gln Gly Gln Leu Met
            100                 105                 110
Ser Val Ser Val Pro Val Asn Thr Leu Val Ile Asp Thr Leu Ser Pro
        115                 120                 125
Thr Ser Trp Gln Ala Ser Ser Phe Phe Val Arg Asn Gly Ser Asn Pro
        130                 135                 140
Glu Gln Asp Pro Leu Arg Asn Leu Ser Gly Gln Ala Val Thr Arg Val
145                 150                 155                 160
Val Gly Gly Met Ser Thr His Trp Thr Cys Ala Thr Pro Arg Phe Asp
                165                 170                 175
Arg Glu Gln Arg Pro Leu Leu Val Lys Asp Asp Gln Asp Ala Asp Asp
            180                 185                 190
Ala Glu Trp Asp Arg Leu Tyr Thr Lys Ala Glu Ser Tyr Phe Lys Thr
        195                 200                 205
Gly Thr Asp Gln Phe Lys Glu Ser Ile Arg His Asn Leu Val Leu Asn
210                 215                 220
Lys Leu Ala Glu Glu Tyr Lys Gly Gln Arg Asp Phe Gln Gln Ile Pro
225                 230                 235                 240
Leu Ala Ala Thr Arg Arg Ser Pro Thr Phe Val Glu Trp Ser Ser Ala
                245                 250                 255
Asn Thr Val Phe Asp Leu Gln Asn Arg Pro Asn Thr Asp Ala Pro Asn
            260                 265                 270
Glu Arg Phe Asn Leu Phe Pro Ala Val Ala Cys Glu Arg Val Val Arg
        275                 280                 285
Asn Thr Ser Asn Ser Glu Ile Glu Ser Leu His Ile His Asp Leu Ile
        290                 295                 300
Ser Gly Asp Arg Phe Glu Ile Lys Ala Asp Val Phe Val Leu Thr Ala
305                 310                 315                 320
Gly Ala Val His Asn Ala Gln Leu Leu Val Asn Ser Gly Phe Gly Gln
                325                 330                 335
Leu Gly Arg Pro Asp Pro Ala Asn Pro Pro Gln Leu Leu Pro Ser Leu
            340                 345                 350
Gly Ser Tyr Ile Thr Glu Gln Ser Leu Val Phe Cys Gln Thr Val Met
        355                 360                 365
Ser Thr Glu Leu Ile Asp Ser Val Lys Ser Asp Met Ile Ile Arg Gly
        370                 375                 380
Asn Pro Gly Asp Leu Gly Tyr Ser Val Thr Tyr Thr Pro Gly Ala Glu
385                 390                 395                 400
Thr Asn Lys His Pro Asp Trp Trp Asn Glu Lys Val Lys Asn His Met
                405                 410                 415
Met Gln His Gln Glu Asp Pro Leu Pro Ile Pro Phe Glu Asp Pro Glu
            420                 425                 430
Pro Gln Val Thr Thr Leu Phe Gln Pro Ser His Pro Trp His Thr Gln
```

|   |   |   |   |   |   |   |   |   |   |   |   |   |   |   |
|---|---|---|---|---|---|---|---|---|---|---|---|---|---|---|
|   |   |   |   | 435 |   |   |   | 440 |   |   |   | 445 |   |   |
| Ile | His | Arg | Asp | Ala | Phe | Ser | Tyr | Gly | Ala | Val | Gln | Gln | Ser | Ile | Asp |
|   | 450 |   |   |   |   | 455 |   |   |   | 460 |   |   |   |   |
| Ser | Arg | Leu | Ile | Val | Asp | Trp | Arg | Phe | Phe | Arg | Thr | Glu | Pro | Lys |
| 465 |   |   |   |   | 470 |   |   |   | 475 |   |   |   |   | 480 |
| Glu | Glu | Asn | Lys | Leu | Trp | Phe | Ser | Asp | Lys | Ile | Thr | Asp | Thr | Tyr | Asn |
|   |   |   |   | 485 |   |   |   |   | 490 |   |   |   |   | 495 |
| Met | Pro | Gln | Pro | Thr | Phe | Asp | Phe | Arg | Phe | Pro | Ala | Gly | Arg | Thr | Ser |
|   |   |   | 500 |   |   |   | 505 |   |   |   |   | 510 |   |   |
| Lys | Glu | Ala | Glu | Asp | Met | Met | Thr | Asp | Met | Cys | Val | Met | Ser | Ala | Lys |
|   |   | 515 |   |   |   |   | 520 |   |   |   |   | 525 |   |   |
| Ile | Gly | Gly | Phe | Leu | Pro | Gly | Ser | Leu | Pro | Gln | Phe | Met | Glu | Pro | Gly |
|   | 530 |   |   |   |   | 535 |   |   |   | 540 |   |   |   |   |
| Leu | Val | Leu | His | Leu | Gly | Gly | Thr | His | Arg | Met | Gly | Phe | Asp | Glu | Gln |
| 545 |   |   |   |   | 550 |   |   |   | 555 |   |   |   |   | 560 |
| Glu | Asp | Lys | Cys | Cys | Val | Asn | Thr | Asp | Ser | Arg | Val | Phe | Gly | Phe | Lys |
|   |   |   | 565 |   |   |   |   | 570 |   |   |   | 575 |   |
| Asn | Leu | Phe | Leu | Gly | Gly | Cys | Gly | Asn | Ile | Pro | Thr | Ala | Tyr | Gly | Ala |
|   |   |   | 580 |   |   |   | 585 |   |   |   |   | 590 |   |   |
| Asn | Pro | Thr | Leu | Thr | Ala | Met | Ser | Leu | Ala | Ile | Lys | Ser | Cys | Glu | Tyr |
|   |   | 595 |   |   |   |   | 600 |   |   |   |   | 605 |   |   |
| Ile | Lys | Asn | Asn | Phe | Thr | Pro | Ser | Pro | Phe | Thr | Asp | Gln | Ala | Glu |
|   | 610 |   |   |   | 615 |   |   |   |   | 620 |   |   |   |

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

TGTAGCTCTC AAACAACGCC CATATGTCTA CTAGCTCGAG CGACCC        46

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

ACTAAGCAAG GTCAGCGAGC CATATGTCAC TCAGCCTGAT CTGTGA        46

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

TGCCGCCGCT GCCTGGTCCC CATATGAAAG TCCCTGGAAT GGACAT        46

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

```
ACRTCRTA Y T TDATRTCCAT                                                        20
```

( 2 ) INFORMATION FOR SEQ ID NO:7:

( i ) SEQUENCE CHARACTERISTICS:
        ( A ) LENGTH: 187 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

```
AATTCGGTAC  CGGATCCGCT  AGCTTTACAT  TATGCTTCCG  GCTCGTATAA  TGTGTGGAAT      60
TGTGAGCGGA  TAACAATTTC  ACACAGGAGG  TTTCATATGC  ATTGATCATT  AATTAATAGC     120
CCGCCTAATG  AGCGGGCTTT  TTTTACTAG   TAGATCTCTG  GCCGTCGTTT  TACAGTCGAC     180
GGTACCG                                                                    187
```

( 2 ) INFORMATION FOR SEQ ID NO:8:

( i ) SEQUENCE CHARACTERISTICS:
        ( A ) LENGTH: 187 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

```
AATTCGGTAC  CGTCGACTGT  AAAACGACGG  CCAGAGATCT  ACTAGTAAAA  AAAAGCCCGC      60
TCATTAGGGG  GGCTATTAAT  TAATGATCAA  TGCATATGAA  AGCTCCTGTG  TGAAATTGTT     120
ATCCGCTCAC  AATTCCACAC  ATTATACGAG  CCGGAAGCAT  AATGTAAAGC  TAGGGGATCC     180
GGTACCG                                                                    187
```